United States Patent

Lai

[19]

[11] Patent Number: 6,115,445
[45] Date of Patent: Sep. 5, 2000

[54] PROGRESSIVE CORRECTION OF RING ARTIFACTS IN A COMPUTED TOMOGRAPHY SYSTEM

[75] Inventor: Ching-Ming Lai, Wakefield, Mass.

[73] Assignee: Analogic Corporation, Peabody, Mass.

[21] Appl. No.: 09/228,372

[22] Filed: Jan. 12, 1999

[51] Int. Cl.[7] ................................................. H61B 6/03
[52] U.S. Cl. ............................. 378/4; 378/901; 382/131
[58] Field of Search .......................... 378/4, 15, 19, 378/901; 382/131

[56] References Cited

U.S. PATENT DOCUMENTS

| 4,670,840 | 6/1987 | Freundlich | 364/414 |
|---|---|---|---|
| 4,891,829 | 1/1990 | Deckman et al. | 378/4 |
| 5,745,542 | 4/1998 | Gordon et al. | 378/4 |
| 5,774,519 | 6/1998 | Lindstrom et al. | 378/18 |
| 5,835,618 | 11/1998 | Fang et al. | 382/132 |

OTHER PUBLICATIONS

Kowalski, "Suppression of Ring Artifacts in CT Fan–Beam Scanners," IEEE Transaction on Nuclear Science, pp. 1111–vol. NS–25, No. 5, Oct. 1978.

*Primary Examiner*—David V. Bruce
*Attorney, Agent, or Firm*—McDermott, Will & Emery

[57] ABSTRACT

In a method and apparatus for progressive correction of ring artifacts in a computed tomography system, multiple-channel ring artifacts are mitigated or eliminated along with single-channel ring artifacts. Detector channels are iteratively grouped into various size groupings, for example, pairs, and the offset error values of each detector channel grouping are determined. The error values corresponding to each detector channel are accumulated at each iteration, and the final accumulated values are applied to captured projection data. In this manner, ring artifacts can be eliminated from the image in just a few iterations.

46 Claims, 7 Drawing Sheets

PROGRESSIVE CORRECTION OF RING ARTIFACTS IN A COMPUTED TOMOGRAPHY SYSTEM

BACKGROUND OF THE INVENTION

In an X-ray computed tomography system, an energy source irradiates X-ray beams through an object, and a detector array senses and measures the intensity of the attenuated X-ray across a thin section of the object. The X-ray intensity level incident at each detector is digitized and converted to a value representing the line integral, referred to in the art as a "projection", of the object along the X-ray path.

Figure 1:
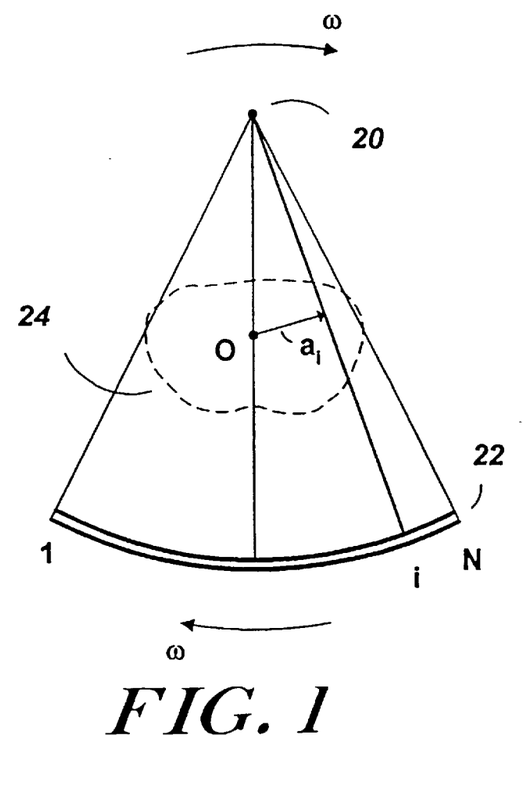
FIG. 1 is a block diagram of a conventional X-ray CT scanner, including an X-ray source and a detector array mounted on a gantry and rotatable about an object at a constant angular velocity of $\omega$, illustrating the distance $a_i$ from the rotation center O to the X-ray incident on detector i.

For third generation systems, during a scan, the X-ray source 20 and the detector array 22 rotate together about the object 24 as shown in FIG. 1. At each rotation angle, or view angle, the collected projections represent a projection profile of the object at that angle. With a set of projection profiles over many view angles, an image of the object across the scanning section can be generated in a process known as reconstruction.

Each detector channel in the array comprises an X-ray detector and associated electronic circuitry for signal amplification and digitization. The channels are manufactured and calibrated to optimize accuracy and uniformity with respect to offset, gain, and linearity. However, even with perfect calibration, the sensitivity of each channel can be altered over time due to variation in temperature, radiation damage, and other physical conditions. Each channel therefore can exhibit an inherent error in its measurement, which can be categorized as an offset error $e_i$ in the projection value of a channel. When the intensity of the offset error $e_i$ of a channel i exceeds that of adjacent channels to a certain degree, a ring artifact is manifested in the reconstructed image. In this manner, the offset error $e_i$ is a ring-causing error.

Figure 2:
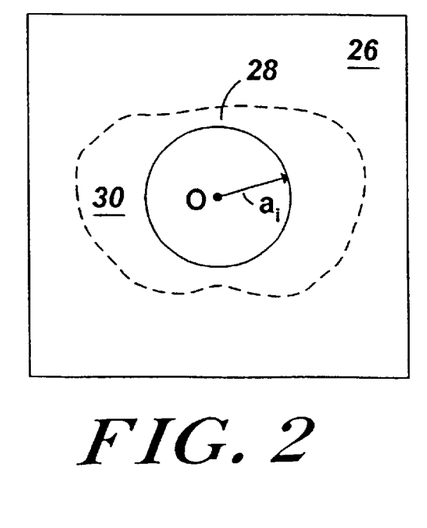
FIG. 2 is a reconstructed image including a concentric ring artifact of radius $a_i$ measured from the rotation center O, as a result of offset error inherent in detector channel i.

The radius $a_i$ of a ring artifact 28 caused by channel i is equal to the distance between the projection path of the corresponding channel i and the center of rotation O, as shown in FIG. 2. Assuming this relationship, a ring artifact in an image can be identified by its corresponding channel number i. Assuming that channels are mutually independent, the offset error $e_i$ amplitudes are randomly distributed among all channels. For a given channel, the offset error $e_i$ may vary as a function of the projection amplitude. Its dependence on the projection amplitude usually remains the same within the duration of a scan. In principle, each affected channel produces a ring artifact of one channel in width, but only those channels with a sufficiently large offset $e_i$ generate visible ring artifacts in the image. With a random distribution of offset error $e_i$, the visible rings are likewise randomly distributed.

In conventional techniques for mitigating offset error, the offset error $e_i$ can be estimated from the projection data, based on the assumptions that the same degree of error occurs over successive view angles, and that the error is independent of the performance of adjacent channels. Furthermore, it is known that the projection data vary gradually as a function of detector channel. Therefore, if projection data are plotted as two-dimensional data (channel number vs. view angle), a low-pass filter can be employed to average the projection values over a number of successive view angles. A high-pass filter can then be applied along the channel number dimension to filter offset error out of the object's projection profile. Linear filtering alone may be insufficient for separating the offset error from the object profile. Therefore, additional nonlinear filtering is often necessary to discriminate offset error from the object profile.

In the conventional techniques, the error offset responsible for causing a single-channel ring can be estimated with fair accuracy. The estimated error is then subtracted from the projection values collected at that channel. Following correction of all channels, the reconstructed image is free of single-channel rings. However, it is quite common for an image to exhibit multiple-channel ring artifacts. The high-pass filter is incapable of yielding an adequate estimate of this multiple-channel error, because such a filter is designed for determining single-channel error. Consequently, multiple-channel rings are not fully corrected, and the resulting image therefore includes reminiscent rings.

In principle, the wider multiple-channel rings are unlikely to occur if the detector channel offset errors are completely independent of each other. However, detectors located in proximity tend to stay in the same physical condition and their corresponding offsets tend to drift together, particularly in a system having solid-state detectors. The intensities of wide multiple-channel rings are generally much weaker than those of the single-channel rings, since the common offset error over multiple-channels is, on average, smaller than a single-channel offset error. Furthermore, as a result of high-pass filtering in the convolution operation performed during the reconstructing process, the intensity of the wide ring artifact does not stand out as much as that of a single-channel ring of the same offset error amplitude. The presence of wide rings is often visible in images of objects of uniform structure, such as water phantoms. However, due to their relatively low intensity, they are less visible in an image of a non-uniform object, for example, human body images.

In principle, existing filtering ring artifact correction techniques can be extended to correct for the wide rings. However, conventional filters are specifically designed to filter out single-channel error. In order to filter out rings of variable multiple-channel width, a set of filters are required, each tailored to handle a specific width. Since a ring can be several channels in width, the total amount of computations required may be several times that needed for single-channel ring correction, leading to an impractical computing time. It is also questionable whether such a solution would lead to effective correction of wide rings, and worse, it is quite possible that this technique of curing the wide ring artifacts may reintroduce narrow ring artifacts back into the image.

Considering the aforementioned problems, little has been done to address the correction of wide rings in the past. The intensity of these wide rings are not as strong as single-channel rings, and with accurate and frequent calibration, they do not pose a serious problem. However, as systems improve and become increasingly sophisticated, it is desirable to be able to correct them. If they are correctable, the requirements for calibration can also be relaxed.

SUMMARY OF THE INVENTION

The present invention is therefore directed to a method and apparatus for progressive correction of ring artifacts in a computed tomography system in a manner which overcomes the limitations of the conventional techniques.

The method of the invention is directed to a technique for correction of a mixture of ring artifacts of various channel widths in an object image generated by a computed tomography system having an array of detector channels for capturing projection data of an object. The method comprises iteratively grouping the detector channels into detector channel groupings. During each iteration, offset error values of each detector channel grouping with respect to other detector channel groupings are determined from the captured projection data. The offset error values are then used to correct the captured projection data.

In a preferred embodiment, adjacent detector channels are grouped into pairs at each iteration. Thus, for example, during the first iteration, each detector channel is grouped individually, and the offset error value of each detector channel determined individually, with respect to other detector channels. During a second iteration, adjacent detector channels are grouped into pairs, and the offset error values of each detector channel pair are determined, with respect to other detector channel pairs. During a third iteration, pairs of adjacent detector channels are paired into quartets, and the offset error values of each quartet are determined, with respect to other detector channel quartets. During a fourth iteration, quartets of adjacent detector channels are paired into octets, and offset error values of each octet are determined, with respect to other detector channel octets. Subsequent iterations may be performed, depending on the total number of detectors used. In alternative embodiments, the number of adjacent channels in each group can be increased in each subsequent iteration, in accordance with other progressions.

At each iteration, the offset error values corresponding to each channel are accumulated. The accumulated values corresponding to each detector channel are applied to the projection data collected by the channel for correction of the captured projection data. The step of determining the offset errors preferably comprises low-pass filtering the data of each detector channel grouping over multiple successive view angles, and high-pass filtering the low-pass filtered data of adjacent channel groupings.

BRIEF DESCRIPTION OF THE DRAWINGS

The foregoing and other objects, features and advantages of the invention will be apparent from the more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF PREFERRED EMBODIMENTS

The present invention is directed to a ring artifact correction technique which employs the same filter to correct for all ring sizes, including both narrow single-channel and wide multiple-channel rings, in an iterative and progressive manner.

Figure 7:
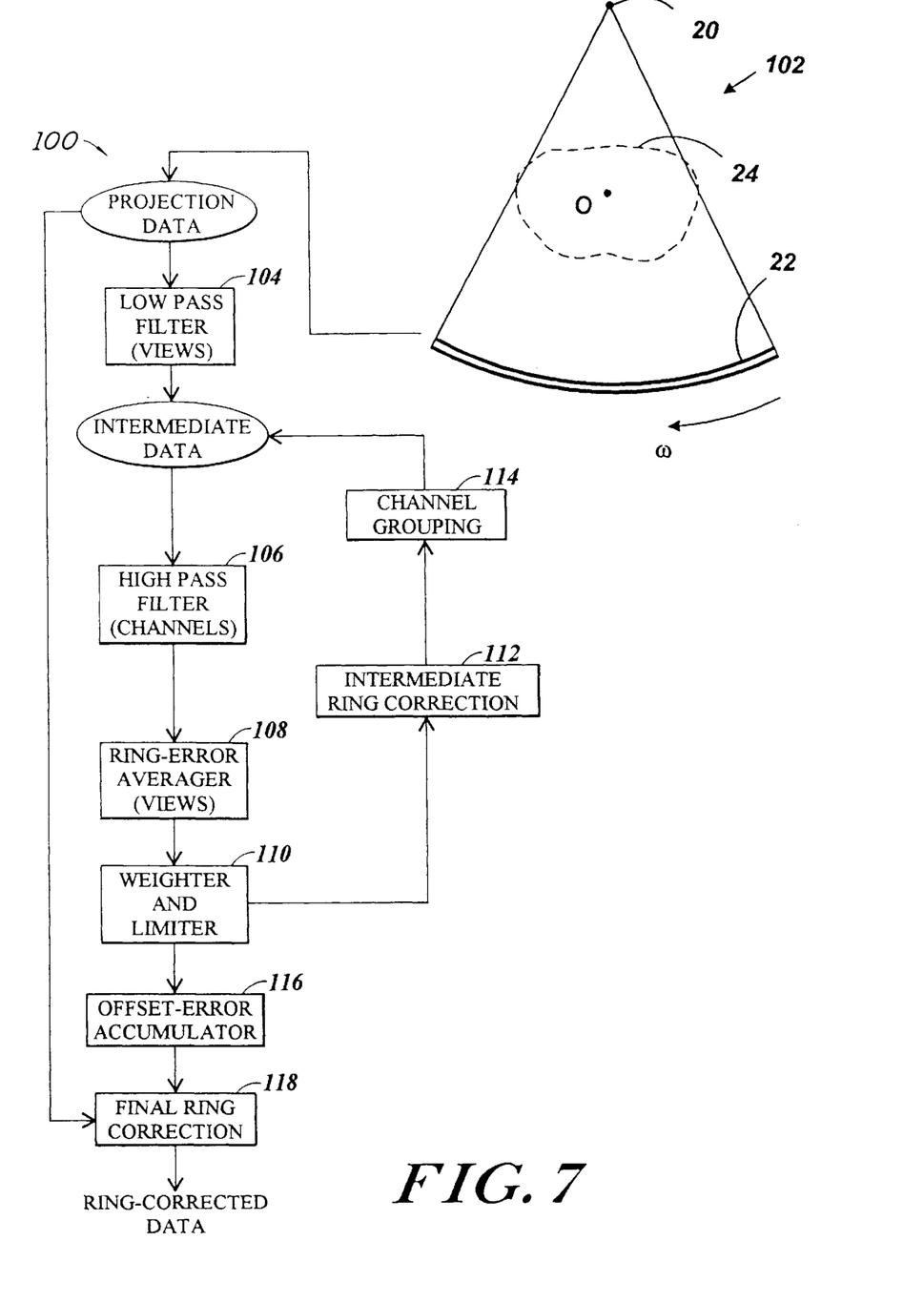
FIG. 7 is a block diagram of a system for progressive ring correction, in accordance with the present invention.

A block diagram of a preferred embodiment of a system 100 for progressive ring correction is shown in FIG. 7, in accordance with the present invention. The system 100 includes a CT scanner 102, including an X-ray source 20 and a detector array 22, mounted on a gantry rotatable about the object 24 for capturing projection data of the object. The projection data are preferably filtered over the view angle by a low-pass filter 104 and over the detector channels by a high-pass filter 106. The filtered results are averaged over many view angles by a ring-error averager unit 108 to generate approximate ring errors, and modified by a weighting and limiting unit 110 to generate detector system offset errors. The offset errors are used by a ring correction unit 112 to correct the intermediate data, which are then progressively re-grouped by a channel grouping unit 114 for the next iteration of ring correction. The offset errors calculated at each iteration are summed at an accumulator 116 in accordance with the original channels. After the last iteration, the accumulated offset errors are presented to a final ring correction unit 118 to correct the original projection data, thereby providing ring-corrected data.

In a preferred embodiment, a single-channel correction is initially performed, in which the data of the various N channels are corrected to eliminate single-channel rings. Every two adjacent channels of the corrected data are then grouped into pairs and treated as a single channel. The total number of channels is thus reduced to N/2 for the next correction iteration (referred to herein as a "pass"), and both channels in each pair are corrected by the same offset error. The second corrected data of N/2 channels are further grouped into N/4 channels to generate third corrected data, and so forth. The offset errors determined at each correction pass are retained and accumulated for each channel. The accumulated offset errors are applied as a correction value to the original data of N channels. Although a 2-to-1 grouping, and four iterations, are spelled out below in describing the preferred embodiment, other groupings, and other numbers of iterations are equally applicable to the present invention.

For simplicity, it is preferred to use the same filter for all correction passes as described above. However, it is not necessary to do so. In principle, the optimal filter in each subsequent pass is nearly, but not exactly, the same as the filter of the first pass. Thus, it is also possible to use a different filter for each pass, and obtain slightly improved results.

A determination of the exact magnitude of the multiple-channel offset error is not necessary for full removal of ring artifacts. A wide ring is gradually corrected over successive correction passes. After a number of passes, the offset error may still not be fully corrected. However, so long as the error varies smoothly across the boundary between adjacent multiple-channels, the ring artifact will not appear. In an experimental embodiment, it has been determined that following a fourth correction pass, with data grouped into N/8 channels, accumulated offset errors are adequate to remove all sizes of visible rings. In this manner, ring artifacts can be eliminated from the image in just a few iterations.

Figure 3A:
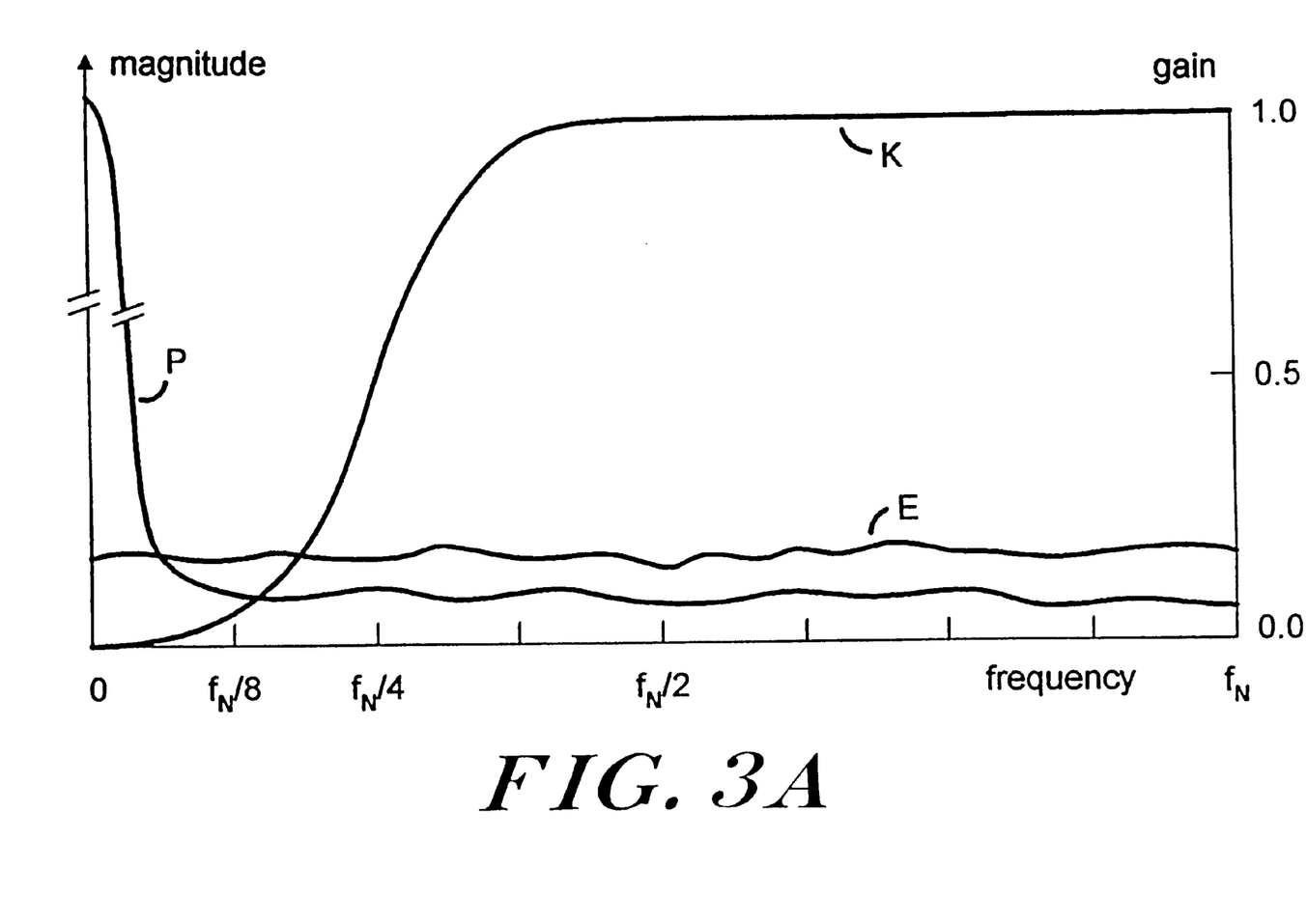
FIG. 3A is an example of a plot of the spectrum of the object profile P and the spectrum of offset errors E, following averaging over a plurality of adjacent view angles, and the frequency response function K of the high-pass filter for progressive correction in accordance with the present invention.

The operation of the progressive correction method of the present invention is best explained in the frequency domain in a qualitative manner, such as the example shown in FIG. 3A, which includes the spectrum of a pure object profile P at a particular view angle, and the spectrum of the associated offset errors E, following averaging over a number of successive view angles. The averaging procedure is, in effect, a low-pass filtering process which suppresses high frequency components, and thus the projection profile P is highly skewed to the low frequency end of the spectrum, as shown. In order to illustrate the high-frequency components at low amplitudes, the vertical scale of the FIG. 3A plot is sectioned to indicate that the magnitude of the projection profile P near zero frequency is much greater than the magnitude appearing on the plot. Also, the offset error values which superimpose on the object profile P in the collected projection data are plotted separately to illustrate the progress of these two components, P and E, in subsequent filtering.

The projection data are collected at N channels, with frequency ranging from 0 to the Nyquist frequency $f_N$. The gain of the frequency response function of the high-pass filter ranges between 0 and 1 as shown in graph K. The high-pass filter in the example given has a half-response point at approximately the one-quarter Nyquist frequency $f_N/4$. The operation of the high-pass filter is the equivalent of multiplying the object profile P and offset error profile E by the filter response function K in frequency space.

Figure 3B:
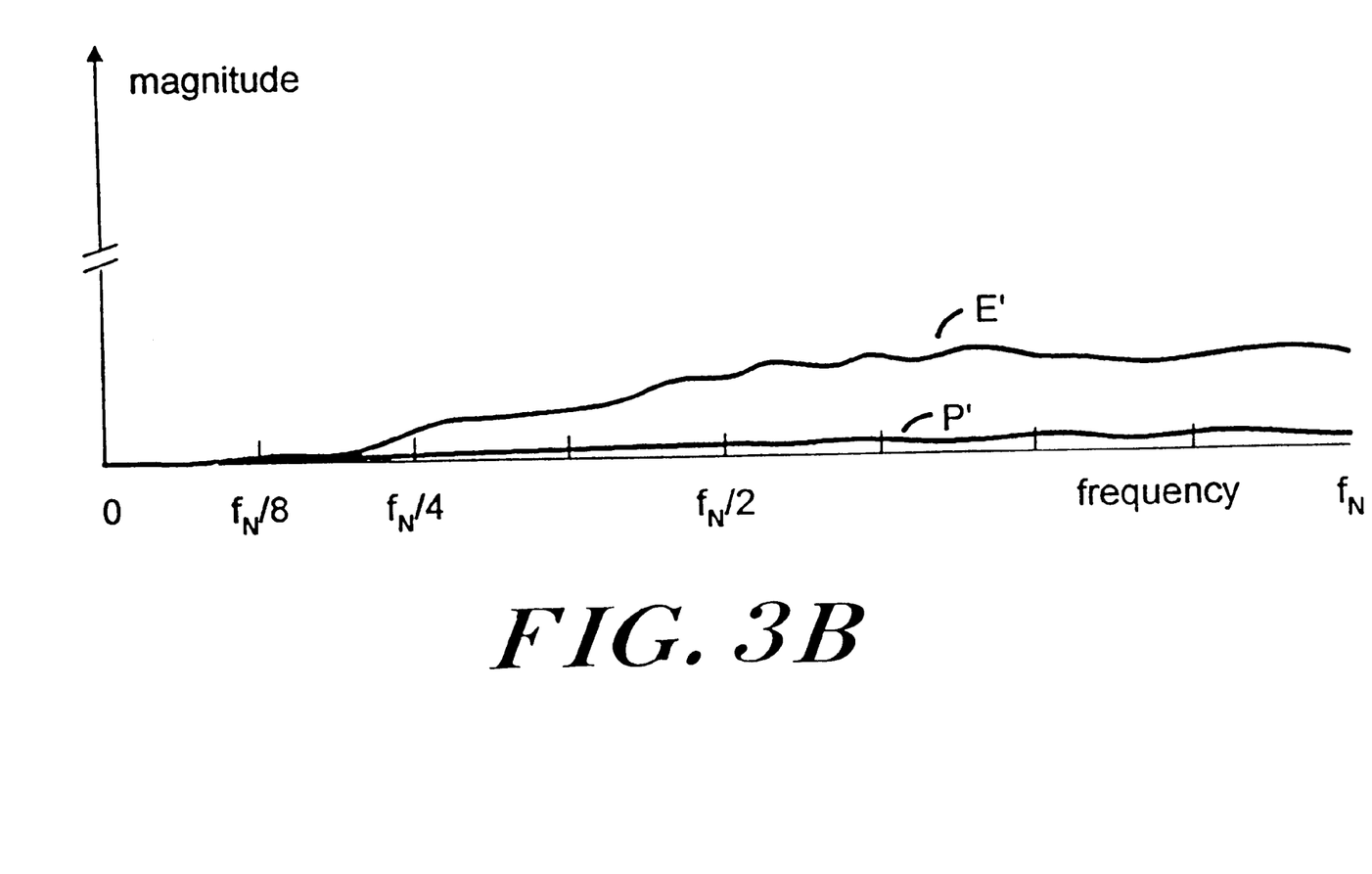
FIG. 3B is an example of a plot of the spectrum of the object profile E' and the offset error P', following first pass high-pass filtering and further averaging over all views in an angular sector in accordance with the present invention.

To reduce the number of computations, it is preferable, although not necessary, to divide the 360° angular range into a number of sectors, each extending over a constant sector angle. A preferred sector angle is between 15° and 30°. The output data of high-pass filtering, including the object profile P and the error offset profile E are then further averaged over the view angles within each angular sector. The spectra of P' and E' of this further-averaged result for an angular sector are shown in FIG. 3B. Because of the additional averaging, the high-pass filtered object profile P', which varies with the view angle in both positive and negative amplitudes, is further diminished to a very small magnitude. On the other hand, the offset error E', which should maintain at a fairly constant level within the angular sector for each channel, is not diminished by further averaging. Thus, the resultant error offset profile E' of FIG. 3B is approximately the product of graphs E and K of FIG. 3A.

The result obtained in the first pass is actually the filtered object profile P' superimposed with the offset error E' in the spatial domain. Since the magnitude of filtered object profile P' is very small, it may be ignored, and the superimposed result may be considered as an estimate for E'. However, this is only an approximation. Depending on the scanning object, the filtered object profile P' may not be sufficiently filtered out. Thus, in a preferred embodiment, the amount of this residual filtered object profile P' is evaluated and used as the basis for adjusting the estimation of the offset error. The spectrum of the adjusted estimates of the offset error departs slightly from the spectrum shown in E'. When these adjusted estimates are used to correct for the collected projection data, the reconstructed image becomes free of single-channel rings.

Figure 4A:
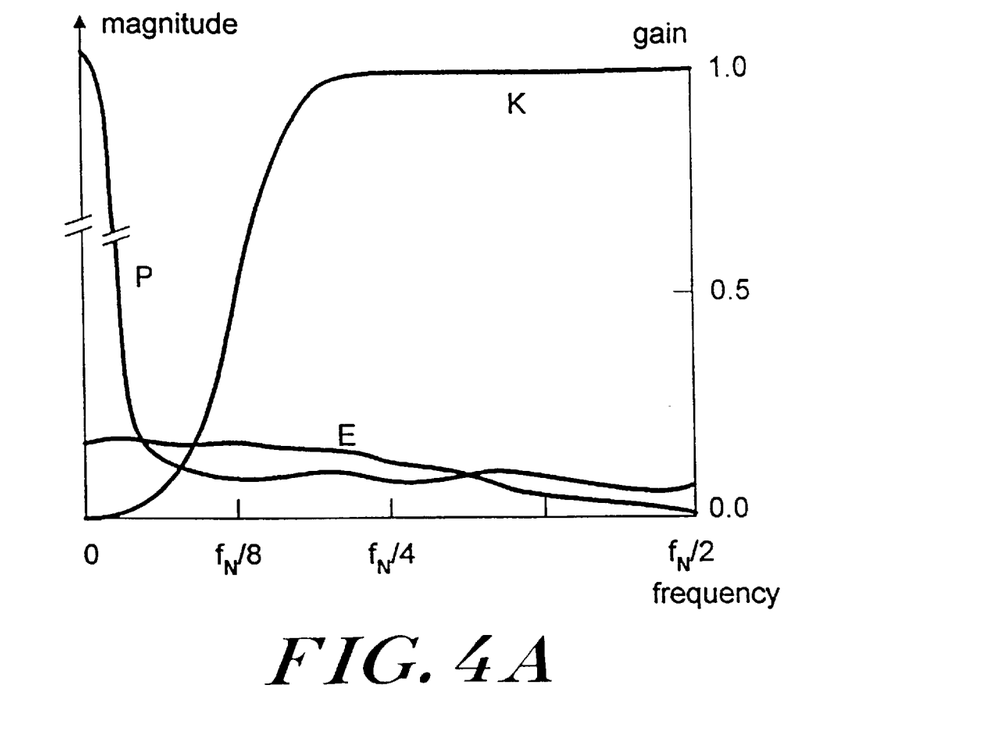
FIG. 4A is an example of a plot of the spectra of the object profile P, the offset error E, and the filter response K at a particular view angle for a second pass, in accordance with the present invention.
Figure 4B:
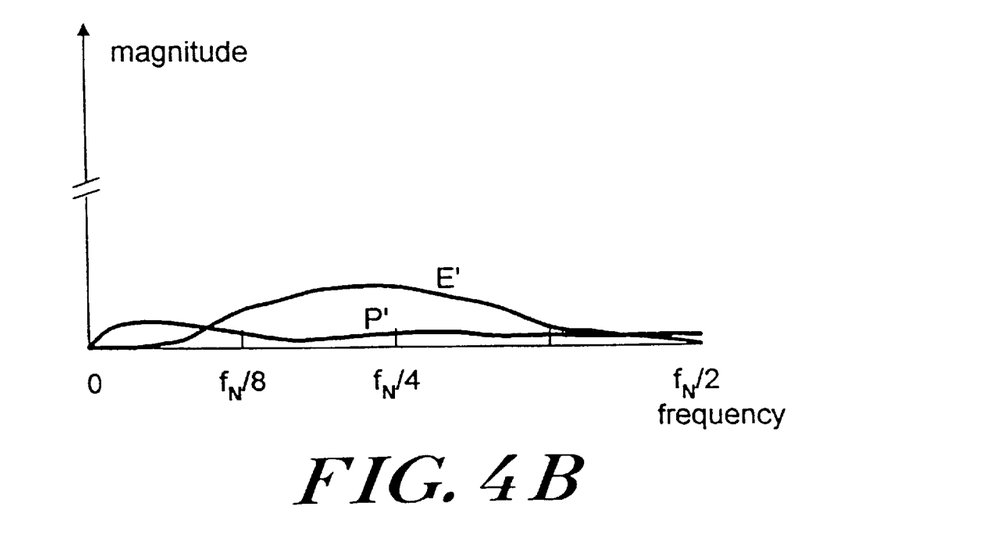
FIG. 4B is an example of a plot of the spectra of the filtered and further averaged object profile P' and the offset errors E' in an angular sector as a result of the second pass in accordance with the present invention.
Figure 5A:
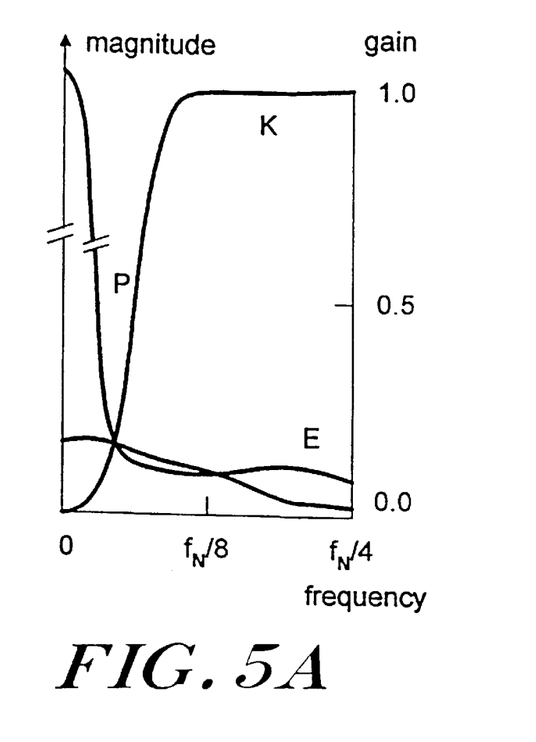
FIG. 5A is an example of a plot of the spectra of the object profile P, the offset errors E, and the filter response K at a view angle for the third pass in accordance with the present invention.
Figure 5B:
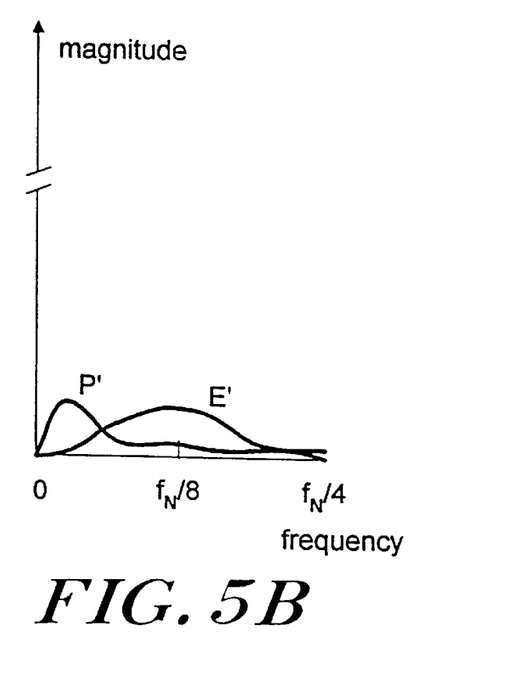
FIG. 5B is an example of a plot of the spectra of the filtered and further averaged object profile P' and offset errors E' in an angular sector as a result of third pass in accordance with the present invention.

In the progressive method of the present invention, following the first pass correction, the first pass corrected data are grouped for a second correction. The grouping is analogous to a re-sampling of the data, in which the data of every two channels in a pair are averaged into a single channel, and the frequency bandwidth is reduced into half of the original Nyquist frequency $f_N/2$. FIG. 4A is a plot of the spectra of the grouped data of the second pass for the object profile P and offset error profile E. The total number of channels is reduced to N/2. The high-pass filter K is likewise compressed by a factor of two, with the half-response point reduced to the location near $f_N/8$ in re-sampled frequency space. The result of the high-pass filter and further averaging over all view angles in a sector is shown in FIG. 4B. The residual filtered object profile P' of the second pass in FIG. 4B is slightly larger than that of the first pass in FIG. 3B, because the spectrum of the object profile P remains roughly the same within this re-sampled frequency range, while the half-response point of the high-pass filter K is shifted to a lower frequency. As will be described below, further methods may be employed to differentiate the offset error profile E further from the object profile P, and thus provide additional basis for improved estimation of the offset error.

Using the results of the second pass correction, the projection data can preferably be re-sampled for third and fourth pass corrections. The spectra of the re-sampled data, as well as the high-pass filtered and further averaged results are given in FIG. 5 for the third pass, in the same manner as in FIG. 4. Again, the primary difference, beside the frequency range, is that the magnitude of the residual-filtered object profile P' becomes larger in the third and fourth passes.

Figure 6:
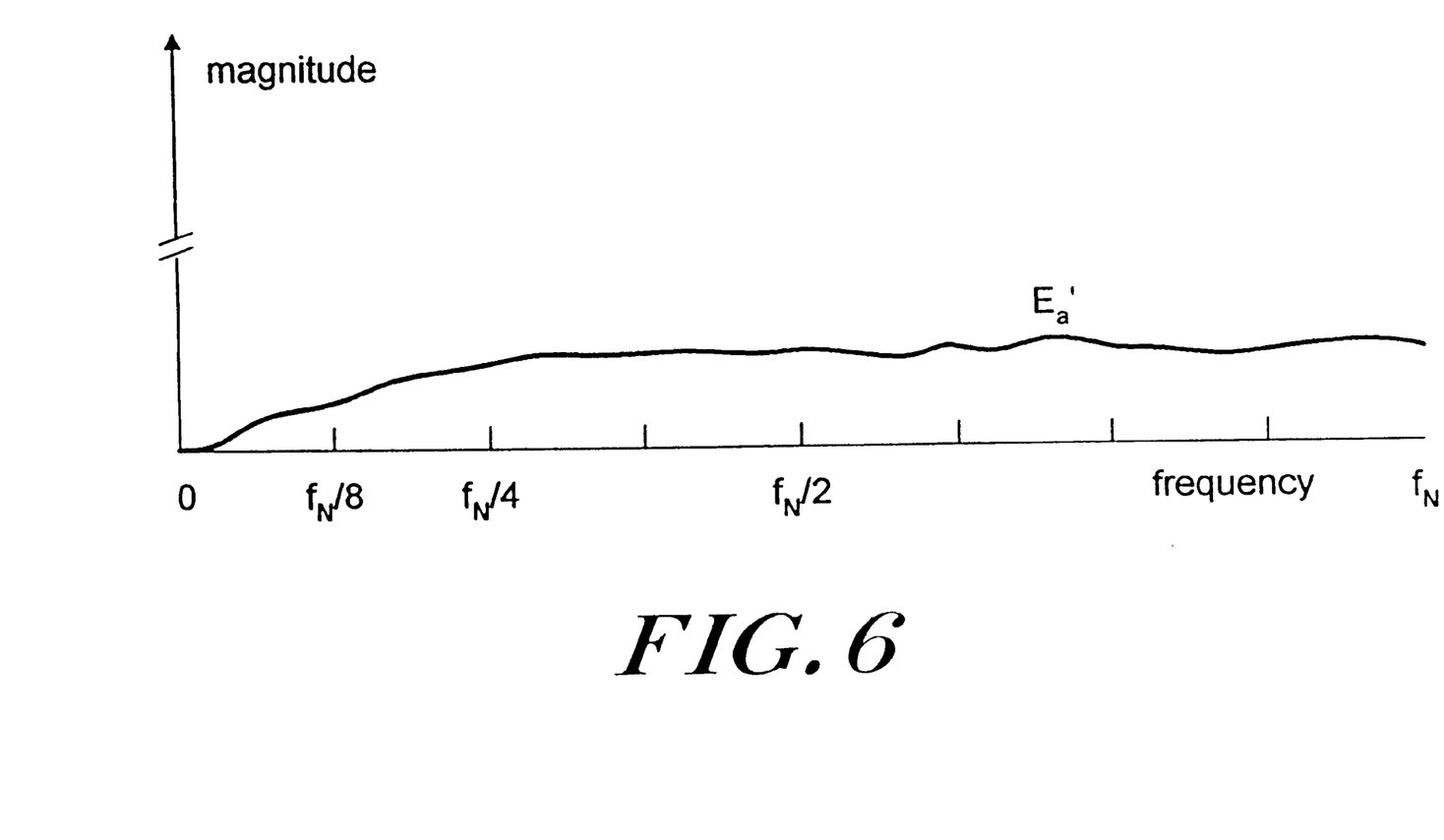
FIG. 6 is an example of a plot of the spectrum of the offset errors $E_a'$, accumulated from four passes, for N original channels in accordance with the present invention.

The estimated offset errors E' generated at each pass are combined in an accumulated offset error value for each of the N channels. The data corresponding to each paired or grouped channel of the second, third, and fourth passes are mapped into two, four, and eight channels, respectively, of this accumulated offset error. An example spectrum of the accumulated offset error $E_a'$ is shown in FIG. 6. It is apparent that the spectrum of this accumulated offset error $E_a'$ is slightly lower in magnitude in the low frequency range than the original offset error E of FIG. 3A. This is due to the relatively larger residual-filtered object profile P' in the low frequencies of later passes, which causes an underestimation of the offset errors in the low frequency range. However, as mentioned above, the existence of offset error in the low frequency range is not a problem because it will be suppressed by the subsequent convolution filter. Although the accumulated offset error does not fully estimate the actual offset errors, it is an adequate approximation for correcting ring artifacts of all sizes in the reconstructed image.

The technique for correction of single-channel ring artifacts presented herein is a preferred embodiment for carrying out the invention. Other techniques are equally applicable, including those described in U.S. Pat. No. 5,745, 542 and G. Kowalski, "Suppression of ring artifacts in CT fan-beam scanners", IEEE Vol. NS-25, no. 5, pp. 1111–16, October 1978, each being incorporated herein by reference.

The first step in the ring correction is the application of a low-pass filter to the data of each channel over a number of successive view angles. Since the projection amplitude varies with view angle, while the offset error amplitude remains fairly constant, low pass filtering enhances the offset error against the object profile (analogous to an enhancement of signal-to-noise ratio) for subsequent high-pass filtering. A moving averaging method can be employed to perform the low-pass filtering operation. If $P_i(\theta)$ represents the projection amplitude of the channel i at view angle $\theta$, and $\Delta\theta$ represents an increment of the view angle, the moving averaged projection amplitude $Q_i(\theta)$ can be written as:

$$Q_i(\theta)=(P_i(\theta-K*\Delta\theta)+ \ldots +P_i(\theta-\Delta\theta)+P_i(\theta)+P_i(\theta+\Delta\theta)+ \ldots +P_i(\theta+K*\Delta\theta))/(2K+1), \quad (1)$$

for averaging over 2K+1 view angles, with i=1, 2, ..., N.

A first high-pass filter is then preferably applied to adjacent channels of the averaged projection $Q_i(\theta)$ for each channel at each view angle, in order to filter out the object profile and to leave the offset error intact. A 3-point filter can be employed to generate the first filtered result $R_i(\theta)$ as:

$$R_i(\theta)=-0.5*Q_{i-1}(\theta)+1.0*Q_i(\theta)-0.5*Q_{i+1}(\theta), \quad (2)$$

with i=1, 2, ..., N. The end points $Q_0(\theta)$ and $Q_{N+1}(\theta)$ can optionally be set to $Q_2(\theta)$ and $Q_{N-1}(\theta)$ respectively.

In the region where the projection paths pass through nearly the center of the object and therefore the projection amplitude varies slowly across adjacent channels, the above 3-point filter can adequately filter out the gross structure, which is the low-frequency component of the object profile. However, in regions where the projection paths pass through the boundary of the object, where the projection amplitude decreases rapidly, the first filtered result $R_i(\theta)$ still contains an appreciable amount of the gross structure.

In order to further isolate the offset error from the object profile, a second high-pass filter is applied to further reduce, or filter out, the object profile. A 5-point filter can be employed for this task, and the second filtered output $S_i(\theta)$ which should primarily contain the offset errors, can be calculated as:

$$S_i(\theta)=-0.2*R_{i-2}(\theta)-0.2*R_{i-1}(\theta)+0.8*R_i(\theta)-0.2*R_{i+1}(\theta)-0.2*R_{i+2}(\theta), \quad (3)$$

with i=1, 2, ..., N. The end points of the filter $R_{-1}(\theta)$, $R_0(\theta)$, $R_{N+1}(\theta)$, and $R_{N+2}(\theta)$ can be generated in many different ways. The simplest is set them to 0, since their effect on results is negligible.

The operation of Equations (2) and (3) may optionally be combined into a 7-point filter. Alternatively, a Fourier filtering technique may be employed, in which the Fourier transform of the averaged projection $Q_i(\theta)$ is multiplied by the equivalent response function of the 7-point filter in frequency space.

To simplify and reduce the number of computations, the full range of view angles can be divided into a number of angular sectors, each sector containing L view angles. The inherent offset error associated with each channel is assumed to remain constant within an angular sector. On the other hand, the fine structure of the object profile varies rapidly as a function of view angle. Thus, the offset error $e_i$ associated with channel i can be estimated as the mean of $S_i(\theta)$ over all view angles in the sector. That is:

$$e_i=(S_i(\theta_1)+S_i(\theta_1+\Delta\theta)+S_i(\theta_1+2\Delta\theta)+S_i(\theta_1+(L-1)*\Delta\theta))/L, \quad (4)$$

where $\theta_1$ is the first view angle in that sector, and i=1, 2, ..., N.

Although the mean of $S_i(\theta)$ is an adequate estimate for the offset error $e_i$ in most regions of the projection data, such an estimate introduces at least two potential problems. First, the object may contain high-contrast features, such as bones in a human body. Projection of these features can generate a large amount of high-frequency components in the filtered projections $S_i(\theta)$. Second, the object may include arc-shaped structural features, particularly near the edge of a rounded object, and the projections of these features may happen to fall on the same channels over several view angles. Like the ring-causing offset error, projection of these arcuate structures will stand out in $S_i(\theta)$. In both situations, the mean of $S_i(\theta)$ is not a reliable estimate for offset error. At the same time, it is less important to accurately correct for the offset error in these regions, because the rings are obscured by the high-contrast features or the coincident arc-shape structures. A solution proposed by the present invention is to weight less, or underestimate, the error $e_i$ in these regions.

A weighting factor, $w_i$, reflecting the confidence of estimation, is used to generate the weighted error $e'_i$ as:

$$e'_i=w_i*e_i, \quad (5)$$

with $w_i$ ranging from 0 to 1. The dependence of $w_i$ on the data is not necessarily in a specific form. One technique for determining the weighting factor $w_i$ value is based on the standard deviation of the filtered projections $S_i(\theta)$ of the same channel over the view angles within that sector. If the filtered projections $S_i(\theta)$ contain only offset error, the projection values should remain fairly constant throughout all view angles within the sector. The standard deviation of $S_i(\theta)$ will be near the extreme of 0 in this case. On the other hand, if the filtered projections $S_i(\theta)$ contain projections of high-contrast matters, the values will vary rapidly over large amplitudes, and the standard deviation will be large. Similarly, because the arc-shaped structure does not exactly coincide with a concentric ring, the projection of the arc-shaped structure in $S_i(\theta)$ usually varies gradually over a large range and contributes to a large standard deviation. If the filtered projection values $S_i(\theta)$ remain fairly constant within the sector, which means the structural shape is precisely coincident with the ring, the presence of any ring artifact will be obscured by the structural shape and the less accurate estimation of the error is acceptable. Thus, if the standard deviation of $S_i(\theta)$ is represented by $\sigma_i$, the weighting factor $w_i$ can be calculated as:

$$w_i = 1.0 - \sigma_i/\sigma_{max} \quad \text{for } \sigma_i < \sigma_{max} \quad (6)$$
$$\phantom{w_i} = 0.0 \quad \text{for } \sigma_i \geq \sigma_{max},$$

where $\sigma_{max}$ is a predetermined constant representing the maximum tolerable standard deviation due to the presence of the residual object profile. For normalized projection data, where the maximum amplitude is typically in the range of 5 to 10 for a human image, a preferred value for this parameter is $\sigma_{max}=0.002$.

To determine the standard deviation, $\sigma_i$, let $\epsilon_i$ be the average of squares of $S_i(\theta)$ as:

$$\epsilon_i=(S_i^2(\theta_1)+S_i^2(\theta_1+\Delta\theta)+S_i^2(\theta_1+2\Delta\theta)+S_i^2(\theta_1+(L-1)*\Delta\theta))/L. \quad (7)$$

It is well known that the square of a standard deviation is equal to:

$$\sigma_i^2=\epsilon_i-e_i^2. \quad (8)$$

Although Equation (6) is suitable for formulating the weighting factor $w_i$, it is equally acceptable, and in fact preferable, to calculate the weighting factor as:

$$w_i = 1.0 - \sigma_i^2/\sigma_{max}^2 \quad \text{for } \sigma_i^2 < \sigma_{max}^2 \qquad (9)$$
$$= 0.0 \qquad \text{for } \sigma_i^2 \geq \sigma_{max}^2.$$

By using the square of standard deviation, the sensitivity of the weighting factor $w_i$ is raised with respect to the deviation $\sigma_i$, and the time consuming square-root calculation is avoided.

With a weighting factor $w_i$ calculated from Equation (9) or the like, the weighted error $e'_i$ is computed according to Equation (5), and used to correct for the original projection $P_i(\theta)$ for every view angle within that sector as:

$$P_i'(\theta) = P_i(\theta) - e'_i, \qquad (10)$$

where $\theta = \theta_1, \theta_1 + \Delta\theta, \theta_1 + 2\Delta\theta, \ldots, \theta_1 + (L-1)*\Delta\theta$.

When the entire set of corrected projections $P_i'(\theta)$ are used for reconstruction, the image will be nearly free of single-channel rings. In the present invention, the progressive operation continues to correct for all sizes of rings, and the original projections are not corrected until the final pass, when the multiple-channel offset errors are determined.

To prepare for second pass correction, the averaged projections $Q_i(\theta)$ are corrected by the averaged error $e'_i$ from the first pass as:

$$Q_i'(\theta) = Q_i(\theta) - e'_i, \qquad (11)$$

for every channel at every view angle in the sector. That is, $\theta = \theta_1, \theta_1 + \Delta\theta, \theta_1 + 2\Delta\theta, \ldots, \theta_1 + (L-1)*\Delta\theta$, where $i = 1, 2, \ldots N$. The corrected projections $Q_i'(\theta)$ are next grouped, for example into pairs of two, as:

$$Q2_i(\theta) = 0.5*(Q_{i+i-1}'(\theta) + Q_{i+i}'(\theta)), \qquad (12)$$

where $i = 1, 2, \ldots, N/2$. In this manner, the number of grouped channels is reduced to half of the number of original channels.

The grouped projections $Q2_i(\theta)$ are next filtered by the three-point high-pass filter to provide filtered projections $R_i(\theta)$ as:

$$R_i(\theta) = -0.5*Q2_{i-1}(\theta) + 1.0*Q2_i(\theta) - 0.5*Q2_{i+1}(\theta) \qquad (13)$$

where $i = 1, 2, \ldots, N/2$. The filter of Equation (13), applied during the second pass, is analogous to the filter of Equation (2) of the first pass. The dual-channel errors $e2_i$ are calculated in the same manner as the single-channel errors $e_i$ in Equations (3) and (4), except that the range of the index is reduced by half to $i = 1, 2, \ldots, N/2$.

At each pass, as more channels are combined into each group, the object profile varies more rapidly across adjacent groups. At the same time, the magnitudes of multiple-channel offset errors are smaller than those of single-channel offset errors. The multiple-channel estimate will contain more of the object profile relative to the offset error, particularly in projection data collected for regions near the boundary of the object. For this reason, it is preferred to use an additional weighting factor to de-emphasize those with large errors, as they are more likely derived from the object profile. Therefore, instead of Equation (5), the weighted multiple-channels errors are given by:

$$e2'_i = w_i * w'_i * e2_i, \qquad (14)$$

and, similar to Equation (9), $w'_i$ is calculated from $$w'_i = 1.0 - g_i^2/g_{max}^2 \quad \text{for } g_i^2 < g_{max}^2 \qquad (15)$$
$$= 0.0 \qquad \text{for } g_i^2 \geq g_{max}^2$$

with $$g_i^2 = 0.5*(e2_{i-1}^2 + e2_{i+1}^2) \qquad (16)$$

It is possible to replace $g_i^2$ calculated by Equation (16) with $g_i^2 = e2_i^2$. However, $g_i^2$ calculated by Equation (16) provides a better indicator for the presence of the residual object profile, because the object profile varies more gradually than the offset error over adjacent groups. Thus, when $e2_i^2$ values are averaged with adjacent groups, as in Equation (16), $g_i^2$ is more dependent on the object profile. As a result, $w'_i$ is a more favorable weighting factor, which reduces the estimate for offset error in the presence of the residual object profile. Additional methods for calculating $g_i^2$ are equally applicable, for example, the following three-group averaging:

$$g_i^2 = 0.333*(e2_{i-1}^2 + e2_i^2 + e2_{i+1}^2) \qquad (17)$$

is as acceptable as the calculation of Equation (16), depending on the application.

Like $\sigma_{max}$, the constant $g_{max}$ represents the maximum tolerable amplitude of error estimate due to the presence of the residual object profile. They are of similar magnitude, and it is acceptable to choose $g_{max} = \sigma_{max}$ for purposes of the present invention.

For the third pass of correction, the two-channel grouped projections $Q2_i(\theta)$ are corrected by the weighted multiple-channel errors $e2'_i$ as:

$$Q2_i'(\theta) = Q2_i(\theta) - e2'_i, \qquad (18)$$

for every channel at every view angle in the sector, with $i = 1, 2, \ldots N/2$. The $Q2_i'(\theta)$ data set are then further grouped into pairs in preparation for the third pass, to contain four original channels in each group as:

$$Q4_i(\theta) = 0.5*(Q2_{i+i-1}'(\theta) + Q2_{i+i}'(\theta)), \qquad (19)$$

where $i = 1, 2, \ldots, N/4$.

The four-channel error data $e4_i$ corresponding to the projection data $Q4_i(\theta)$ are calculated in the same manner as the previous pass, with $Q4_i(\theta)$ substituting for $Q2_i(\theta)$ in Equation (13). And, like Equation (14), the weighted four-channel errors are calculated as:

$$e4'_i = w_i * w'_i * e4_i, \qquad (20)$$

with $w_i$ and $w'_i$ given by Equations (9) and (15), and (similar to Equation (16)):

$$g_i^2 = 0.5*(e4_{i-1}^2 + e4_{i+1}^2) \qquad (21)$$

where $i = 1, 2, \ldots, N/4$.

The fourth correction pass is performed in the same manner as the third correction, with $Q8_i(\theta)$ and $e8_i$ replacing $Q4_i(\theta)$ and $e4_i$, respectively, to determine the weighted eight-channel error $e8'_i$ for $i = 1, 2, \ldots, N/8$.

In an experimental embodiment operating on data collected from a CT scanner, it was determined that four correction passes were suitable for ring artifact correction to a satisfactory level. If further correction is desirable, the process can continue to fifth and sixth passes and beyond, depending on the number of detector channels, the number of channels grouped at each pass, and the level of precision required.

It was also determined that an optimal correction can be achieved by applying a scaling factor to the weighted error in each pass. The scaling factor can be considered as a variable, for tuning the high-pass filter and the weighting factors w and w', to obtain best estimate of the offset error in each pass. It was found that the optimal scaling factor is approximately 0.6 for the first pass, and 0.9 for the second, third, and fourth passes. In this case, the calculated values of $e'_i$, $e2'_{i2}$, $e4'_{i4}$, and $e8'_{i8}$ in the above description are replaced by $0.6e'_i$, $0.9e2'_{i2}$, $0.9e4'_{i4}$, and $0.9e8'_{i8}$, respectively. The optimal scaling factor depends on the detector system and the extent of the offset errors.

Suppose that four correction passes are performed. The weighted errors are summed to an accumulated weighted error $E'_i$ at each pass. At the end of fourth pass, the accumulated error $E'_i$ is represented by:

$$E'_i = e'_i + e2'_{i2} + e4'_{i4} + e8'_{i8} \quad (22)$$

for every angular sector in every original channel i=1, 2, . . ., N. The indices for the second pass i2, third pass i4, and fourth pass i8 are, for example, the truncated integers generated by dividing the original channel number by 2, 4, and 8, respectively. That is:

$$i2 = (i-1)/2 + 1 \quad (23)$$
$$i4 = (i-1)/4 + 1$$
$$i8 = (i-1)/8 + 1,$$

with i2=1, 2, . . . , N/2, i4=1, 2, . . . , N/4, and i8=1, 2, . . . , N/8.

Since the intensity of the ring artifact varies gradually from one sector to another, it is preferred that the accumulated weighted error $E'_i$ be interpolated between adjacent angular sectors such as a, b, c. For example, if $Ea'_i$, $Eb'_i$, and $Ec'_i$ represent the accumulated weighted error of channel i in three consecutive sectors, the interpolated correction for the middle sector b will be:

$$P_i'(\theta_1+k\Delta\theta)=P_i(\theta_1+k\Delta\theta)-((0.5-k/L)*Ea'_i+(0.5+k/L)* Eb'_i) \text{ for } 0 \leq k < L/2 \quad (24)$$

and $$P_i'(\theta_1+k\Delta\theta)=P_i(\theta_1+k\Delta\theta)-((1.5-k/L)*Eb'_i+(k/L-0.5)*Ec'_i) \text{ for } L/2 \leq k < L \quad (25)$$

with i=1, 2, . . . , N, for the projection at view angle $\theta=\theta_1+k\Delta\theta$. When all projections are corrected in this manner and the corrected projections $P_i'(\theta)$ are used for the reconstruction, the image will be suitably corrected for all sizes of single-channel and multiple-channel ring artifacts.

The foregoing discussion provides an effective method for correction of all sizes of concentric ring artifacts in the CT images. Experimental results demonstrate adequate removal of all sizes of rings inherent in the data collected from a scanner. A single-channel ring correction procedure is employed repetitively to improve results at each pass. Following the first correction, adjacent channels of corrected data are grouped for the second correction. The grouping and correction passes continue on an iterative basis until wider, multiple-channel rings are progressively corrected to an acceptable level.

In later passes, as more channels are combined into a group for correction, it is more difficult to separate the object profile from the ring-causing offset errors. To address this issue, an additional weighting factor is employed following the first pass to further differentiate the object profile from the offset error.

Since grouping of channels is an averaging process, the magnitude of the offset error and its standard deviation are expected to decrease with each pass, as more channels are combined in a group. Thus, it is preferred to reduce the maximum level $\sigma_{max}$ of the standard deviation in the first weighting factor $w_i$, and $g_{max}$ in the weighting factor $w'_i$ for subsequent passes. For the example given above, it is preferred to use:

$$\sigma_{max2}^2 = \sigma_{max}^2/2 \text{ and } g_{max2}^2 = g_{max}^2/2 \quad \text{for the second pass} \quad (26)$$
$$\sigma_{max4}^2 = \sigma_{max}^2/4 \text{ and } g_{max4}^2 = g_{max}^2/4 \quad \text{for the third pass}$$
$$\sigma_{max8}^2 = \sigma_{max}^2/8 \text{ and } g_{max8}^2 = g_{max}^2/8 \quad \text{for the second pass}$$

instead of $\sigma_{max}^2$ in Equation (9) and $g_{max}^2$ in Equation (15). It is also preferred to limit the averaged error of each pass to a maximum level, such that:

$$e'_i = e'_{max} \quad \text{if} \quad e'_i < e'_{max} \quad (27)$$
$$e2'_{i2} = e2'_{max} \quad \text{if} \quad e2'_{i2} < e2'_{max}$$
$$e4'_{i4} = e4'_{max} \quad \text{if} \quad e4'_{i4} < e4'_{max}$$
$$e8'_{i8} = e8'_{max} \quad \text{if} \quad e8'_{i8} < e8'_{max}$$

where $e'_{max}$, $e2'_{max}$, $e4'_{max}$, and $e8'_{max}$, are the maximum allowable averaged error in the first, second, third, and forth correction passes. In a data collection involving normalized projection data where the maximum amplitude is typically in the range of 5 to 10 for a human image, the value $e'_{max}$ is preferably set to 0.002. The remaining maximum error values can be derived from $e'_{max}$ as:

$$e'_{max} = 0.002 \quad (28)$$
$$e2'_{max} = e'_{max}/\sqrt{2}$$
$$e4'_{max} = e'_{max}/\sqrt{4}$$
$$e8'_{max} = e'_{max}/\sqrt{8}$$

The purpose of the maximum limits is to prevent over correction in which the offset error is over-estimated because of spurious offset error arising from structural features of the object. In other words, it prevents adding an artificial ring into the image as a result of poor estimation.

The averaged error calculated before application of the limiter in Equation (27) is useful for providing an indication of the physical condition of the detector system. The values can be accumulated into an array $C_i$ as $$C_i = e'_i + e2'_{i2} + e4'_{i4} + e8'_{i8} \quad (29)$$

for each original channel i in each sector as in Equations (22) and (23) without limiting the error of each pass to a maximum level. The accumulated condition data $C_i$ can be averaged over all angular sectors to give a single $C_i$ for each original channel i=1, 2, . . . , N. If any value of $C_i$ is substantially higher than $e'_{max}$, this is an indication that the corresponding detecting channel is malfunctioning, or in poor condition. This system operator can be informed of the status, and decide whether to discard data from that channel to be replaced by, for example, interpolated data from adjacent channels.

Although a specific single-channel ring correction technique is given above, as an example, other single-channel correction techniques can be employed as the basis for the progressive correction method of the present invention to correct for multiple-ring artifacts of various widths. However, a similar weighting factor consistent with the alternative technique, may be required to further differentiate the object profile from the offset error.

With a binary grouping, the total number of groups is reduced according to an exponential rate at each successive iteration. Mathematically, the number of computations will never be more than twice the number of computations required for single-channel correction, even if the iterations continue to the extreme where all original channels are combined into a single group. Furthermore, the initial operation of computing a moving average is performed only once, for example prior to the first pass. As an example, if the process stops at the fourth pass, where 8 original channels are grouped for correction, the total computing time for this progressive correction is approximately 1.8 times the computing time of the single-channel ring correction, a reasonable computing time for practical applications.

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A method for correction of multiple-channel ring artifacts in an object image generated by a computed tomography system having an array of detector channels for capturing projection data of an object comprising:
   iteratively grouping the detector channels into detector channel groupings, and determining, from the captured projection data, offset error values of each detector channel grouping with respect to other detector channel groupings; and
   correcting the captured projection data by the offset error values.

2. The method of claim 1 wherein the step of iteratively grouping the detector channels comprises, at a first iteration, grouping each detector channel individually, and determining offset error values of each detector channel individually, with respect to other detector channels.

3. The method of claim 1 wherein grouping the detector channels into detector channel groupings comprises grouping the detector channels into detector channel pairs.

4. The method of claim 3 wherein grouping the detector channels into detector channel pairs further comprises,
   at a first iteration, grouping each detector channel individually, and determining offset error values of each detector channel individually, with respect to other detector channels; and
   at a second iteration, grouping adjacent detector channels into pairs, and determining offset error values of each detector channel pair, with respect to other detector channel pairs.

5. The method of claim 4 wherein grouping the detector channels into detector channel pairs further comprises,
   at a third iteration, pairing adjacent detector channel pairs into quartets, and determining offset error values of each quartet, with respect to other detector channel quartets; and
   at a fourth iteration, pairing adjacent detector channel quartets into octets, and determining offset error values of each octet, with respect to other detector channel octets.

6. The method of claim 1 wherein grouping the detector channels comprises grouping adjacent detector channels into detector channel groupings.

7. The method of claim 1 wherein correcting comprises accumulating, at each iteration, the offset error values corresponding to each channel, and applying the accumulated offset error value corresponding to each channel to projection data collected by the channel.

8. The method of claim 1 wherein correcting further comprises applying the offset error values of each detector channel to future projection data collected by the channel.

9. The method of claim 1 wherein correcting comprises:
   low-pass filtering the data of each detector channel grouping over multiple successive view angles;
   high-pass filtering the low-pass filtered data of adjacent channel groupings.

10. The method of claim 9 wherein low-pass filtering comprises calculating a moving average.

11. The method of claim 9 wherein high-pass filtering comprises a spatial-domain filtering technique selected from the group consisting of: 3-point filter, 5-point-filter, 7-point filter, and a frequency-domain filtering technique by Fourier transform.

12. The method of claim 11 wherein the same filtering technique is used for all iterations.

13. The method of claim 11 wherein different filtering techniques are used in at least two iterations.

14. The method of claim 1 further comprising partitioning the captured projection data into data collected over a sector of view angles.

15. The method of claim 1 further comprising modifying the offset error values by applying data-dependent weighting factors.

16. The method of claim 15 wherein correcting comprises:
   low-pass filtering the data of each detector channel grouping over multiple successive view angles;
   high-pass filtering the low-pass filtered data of adjacent channel groupings; and
   wherein the weighting factors are determined based on the standard deviation, or the square of the standard deviation, of the projection data.

17. The method of claim 15 wherein correcting comprises:
   low-pass filtering the data of each detector channel grouping over multiple successive view angles;
   high-pass filtering the low-pass filtered data of adjacent channel groupings; and
   wherein the weighting factors are determined based on the square, or the averaged square, of the high-pass filtered projection data.

18. The method of claim 1 further comprising modifying the offset error values by applying constant scaling factors.

19. The method of claim 1 further comprising limiting the degree of correction by the maximum average of the offset error values.

20. The method of claim 1 further comprising generating offset error values for recording the status of each individual detector, determining bad detectors from the status, and replacing data of bad detectors with interpolated data from adjacent detectors.

21. A system for correction of multiple-channel ring artifacts in an object image generated by a computed tomography system having an array of detector channels for capturing projection data of an object comprising:

a channel data processor for iteratively grouping the detector channels into detector channel groupings, and for determining, from the captured projection data, offset error values of each detector channel grouping with respect to other detector channel groupings; and a ring correction unit for correcting the captured projection data by the offset error values.

22. The system of claim 21 wherein the channel data processor comprises means for grouping, at a first iteration, each detector channel individually, and means for determining offset error values of each detector channel individually, with respect to other detector channels.

23. The system of claim 21 wherein the channel data processor comprises means for grouping the detector channels into detector channel pairs.

24. The system of claim 23 wherein the channel data processor further comprises:

means for grouping, at a first iteration, each detector channel individually, and means for determining offset error values of each detector channel individually, with respect to other detector channels; and means for grouping, at a second iteration, adjacent detector channels into pairs, and means for determining offset error values of each detector channel pair, with respect to other detector channel pairs.

25. The system of claim 24 wherein the channel data processor further comprises:

means for grouping, at a third iteration, adjacent detector channel pairs into quartets, and means for determining offset error values of each quartet, with respect to other detector channel quartets; and means for grouping, at a fourth iteration, adjacent detector channel quartets into octets, and means for determining offset error values of each octet, with respect to other detector channel octets.

26. The system of claim 21 wherein the channel data processor comprises means for grouping adjacent detector channels into detector channel groupings.

27. The system of claim 21 wherein the ring correction unit comprises means for accumulating, at each iteration, the offset error values corresponding to each channel, and means for applying the accumulated offset error value corresponding to each channel to projection data collected by the channel.

28. The system of claim 21 wherein the ring correction unit further comprises means for applying the offset error values of each detector channel to future projection data collected by the channel.

29. The system of claim 21 wherein the ring correction unit comprises:

a low-pass filter for low-pass filtering the data of each detector channel grouping over multiple successive view angles;

a high-pass filter for high-pass filtering the low-pass filtered data of adjacent channel groupings.

30. The system of claim 29 wherein the low-pass filter comprises means for calculating a moving average.

31. The system of claim 29 wherein the high-pass filter comprises a spatial-domain filter selected from the group consisting of: 3-point filter, 5-point-filter, 7-point filter, and a Fourier transform frequency-domain filter.

32. The system of claim 31 wherein the same filter is used for all iterations.

33. The system of claim 31 wherein different filters are used in at least two iterations.

34. The system of claim 21 further comprising means for partitioning the captured projection data into data collected over a sector of view angles.

35. The system of claim 21 further comprising means for modifying the offset error values by applying data-dependent weighting factors.

36. The system of claim 35 wherein the ring correction unit comprises:

a low-pass filter for low-pass filtering the data of each detector channel grouping over multiple successive view angles;

a high-pass filter for high-pass filtering the low-pass filtered data of adjacent channel groupings; and wherein the weighting factors are determined based on the standard deviation, or the square of the standard deviation, of the high-pass filtered projection data.

37. The system of claim 35 wherein the ring correction unit comprises:

a low-pass filter for low-pass filtering the data of each detector channel grouping over multiple successive view angles;

a high-pass filter for high-pass filtering the low-pass filtered data of adjacent channel groupings; and wherein the weighting factors are determined based on the square, or the averaged square, of the high-pass filtered projection data.

38. The system of claim 21 further comprising means for modifying the offset error values by applying constant scaling factors.

39. The system of claim 21 further comprising means for limiting the degree of correction by the maximum average of the offset error values.

40. The system of claim 21 further comprising means for generating offset error values for recording the status of each individual detector, means for determining bad detectors from the status, and means for replacing the data of bad detectors with interpolated data from adjacent detectors.

41. A system for correction of multiple-channel ring artifacts in an object image generated by a computed tomography scanner having an array of detector channels for capturing projection data of an object comprising a subsystem constructed and arranged so as to iteratively group the detector channels into detector channel groupings, to determine, from the captured projection data, offset error values of each detector channel grouping with respect to other detector channel groupings; and to correct the captured projection data by the offset error values.

42. The system of claim 41 wherein the subsystem further groups, at a first iteration, each detector channel individually, and determines offset error values of each detector channel individually, with respect to other detector channels.

43. The system of claim 41 wherein the subsystem groups the detector channels into detector channel pairs.

44. The system of claim 43 wherein the subsystem further:

groups, at a first iteration, each detector channel individually, and determines offset error values of each detector channel individually, with respect to other detector channels; and groups, at a second iteration, adjacent detector channels into pairs, and determines offset error values of each detector channel pair, with respect to other detector channel pairs.

45. The system of claim 44 wherein the subsystem further:

groups, at a third iteration, adjacent detector channel pairs into quartets, and determines offset error values of each quartet, with respect to other detector channel quartets; and groups, at a fourth iteration, adjacent detector channel quartets into octets, and determines offset error values of each octet, with respect to other detector channel octets.

46. The system of claim 41 wherein the subsystem groups adjacent detector channels into detector channel groupings.

* * * * *